United States Patent
Shibayama et al.

(10) Patent No.: US 8,583,588 B2
(45) Date of Patent: Nov. 12, 2013

(54) METHOD FOR JUDGING RISK OF CANCER RECURRENCE, COMPUTER PROGRAM, AND COMPUTER SYSTEM

(75) Inventors: Masaki Shibayama, Kobe (JP); Hideki Ishihara, Miki (JP); Keigo Gohda, Kobe (JP); Satoshi Nakayama, Kobe (JP); Tadashi Kiniwa, Tokyo (JP)

(73) Assignee: Sysmex Corporation, Hyogo (JP)

( * ) Notice: Subject to any disclaimer, the term of this patent is extended or adjusted under 35 U.S.C. 154(b) by 251 days.

(21) Appl. No.: 13/074,745

(22) Filed: Mar. 29, 2011

(65) Prior Publication Data

US 2011/0246413 A1 Oct. 6, 2011

(30) Foreign Application Priority Data

Mar. 30, 2010 (JP) ................................. 2010-079197

(51) Int. Cl.
*G06F 17/00* (2006.01)
*C12Q 1/68* (2006.01)
*G06F 19/18* (2011.01)

(52) U.S. Cl.
CPC ...................................... *G06F 19/18* (2013.01)
USPC .................... 706/54; 702/19; 435/6

(58) Field of Classification Search
None
See application file for complete search history.

(56) References Cited

U.S. PATENT DOCUMENTS

2003/0225528 A1 12/2003 Baker et al.
2007/0099219 A1* 5/2007 Teverovskiy et al. ............. 435/6
2009/0246809 A1 10/2009 Shibayama et al.

FOREIGN PATENT DOCUMENTS

JP 2005-519624 A 7/2005
JP 2009-232815 A 10/2009
WO 2009/066258 A1 5/2009

OTHER PUBLICATIONS

Mark J Beresford, et al., "Measuring Proliferation in Breast Cancer: Practicalities and Applications", Breast Cancer Research, 2006, pp. 1-11, vol. 8, No. 6.
Soonmyung Paik, et al., "A Multigene Assay to Predict Recurrence of Tamoxifen-Treated, Node-Negative Breast Cancer", The New England Journal of Medicine, Dec. 30, 2004, pp. 2817-2826. vol. 351, No. 27.

* cited by examiner

*Primary Examiner* — Alan Chen
(74) *Attorney, Agent, or Firm* — Sughrue Mion, PLLC (57) ABSTRACT

A method for judging a risk of cancer recurrence comprising: acquiring an activity value and expression level of a first cyclin dependent kinase (CDK) of a cell contained in tissues extracted from cancer patients, an activity value and expression level of a second CDK, and a number of Ki67-expressing cells or an expression level of Ki67; and judging a risk of cancer recurrence based on the acquired activity value and expression level of the first CDK, the activity value and expression level of the second CDK, and a percentage of Ki67-expressing cells or the expression level of Ki67. A computer program product and a computer system are also disclosed.

20 Claims, 6 Drawing Sheets

METHOD FOR JUDGING RISK OF CANCER RECURRENCE, COMPUTER PROGRAM, AND COMPUTER SYSTEM

FIELD OF INVENTION

The present invention relates to a method for judging a risk of cancer recurrence, a computer program, and a computer system.

BACKGROUND

As a method of judging a risk of cancer recurrence, a pathological evaluation method using Ki67 protein contained in cells extracted from cancer patients as a cancer marker is known. For example, there is a correlation between the proportion of the number of Ki67-expressing cells in the number of cells to be measured with the histopathological grade of cancer and the risk of cancer recurrence increases as the proportion of the number of Ki67-expressing cells is higher, which is described in Mark J Beresford, et al., Breast Cancer Research 2006, 8:216. Here, only the Ki67-expressing cells are stained using a reagent which specifically stains Ki67 in the cells so that the proportion of the number of Ki67-expressing cells in total cells is calculated.

Further, a method for judging a risk of recurrence including: analyzing the presence or absence of the expression of 21 gene clusters including ki67 gene; calculating a recurrence score; and classifying the results of the recurrence score into three stages (risk of recurrence is high, medium, or low) is described in N Engl J Med 2004; 351:2817-26.

In N Engl J Med 2004; 351:2817-26, a hazard ratio (HR) calculated using a statistical procedure is shown as an index showing the reliability of the classified results based on the recurrence score, however there is a further need for the judgment method in which the HR is improved.

On the other hand, a method for judging a risk of cancer recurrence using cyclin-dependent kinase (hereinafter also referred to as CDK) is described in United States Patent Application Publication No. 2009/246809. In this method, the risk of recurrence of cancer is judged by comparing a recurrence risk score which is calculated based on activity values and expression levels of two cyclin-dependent kinases (CDKs) with a predetermined threshold value.

SUMMARY

The scope of the present invention is defined solely by the appended claims, and is not affected to any degree by the statements within this summary.

A first aspect of the present invention is a method for judging a risk of cancer recurrence comprising: acquiring an activity value and expression level of a first cyclin dependent kinase (CDK) of a cell contained in tissues extracted from cancer patients, an activity value and expression level of a second CDK, and a number of Ki67-expressing cells or an expression level of Ki67; and judging a risk of cancer recurrence based on the acquired activity value and expression level of the first CDK, the activity value and expression level of the second CDK, and a percentage of Ki67-expressing cells or the expression level of Ki67.

A second aspect of the present invention is a computer program product for enabling a computer to determine cancer recurrence, comprising: a computer readable medium; and software instructions, on the computer readable medium, for enabling the computer to perform predetermined operations, comprising: acquiring an activity value and expression level of a first cyclin-dependent kinase (CDK) of a cell contained in tissues extracted from cancer patients, an activity value and expression level of a second CDK, and a number of Ki67-expressing cells or an expression level of Ki67; and judging a risk of cancer recurrence based on the acquired activity value and expression level of the first CDK, the activity value and expression level of the second CDK, and the percentage of Ki67-expressing cells or the expression level of Ki67.

A third aspect of the present invention is a computer system adapted to determine cancer recurrence, comprising: a processor, and a memory, under control of said processor, including software instructions adapted to enable the computer system to perform operations comprising: acquiring an activity value and expression level of a first cyclin-dependent kinase (CDK) of a cell contained in tissues extracted from cancer patients, an activity value and expression level of a second CDK, and a number of Ki67-expressing cells or an expression level of Ki67; and judging a risk of cancer recurrence based on the acquired activity value and expression level of the first CDK, the activity value and expression level of the second CDK, and a percentage of Ki67-expressing cells or the expression level of Ki67.

DETAILED DESCRIPTION OF THE EMBODIMENT

The judgment method of the present invention includes acquiring the activity values and expression levels of a first cyclin-dependent kinase (CDK) and a second CDK of cells contained in tissues extracted from cancer patients as well as the number and expression level of Ki67; and judging the risk of cancer recurrence based on the obtained activity values and expression levels of the first CDK and the second CDK as well as the expression rate and expression level of Ki67.

The term "recurrence" herein includes the case where after an organ is partially eliminated from a cancer patient for extirpating a malignant tumor, the same malignant tumor reappears in the remaining organ, and the case where a cancerous cell is separated from a primary tumor and carried into a distant tissue (distant organ) and proliferates autonomously therein (metastatic recurrence).

The term "risk of recurrence" herein means the risk of cancer recurrence in the body of a cancer patient and the risk of death of the patient by cancer recurrence. Unless otherwise specified herein, the term "risk of recurrence" includes both the risks.

Tissues extracted from cancer patients may be tissues constituting supporting tissues in body tissues of the patients, such as fibrous connective tissue, cartilage tissue, bone tissue, blood and lymph; epithelium tissue; muscle tissue; nerve tissue; exocrine tissue; and endocrine tissue. Mammary tissue as exocrine tissue present in the breast is preferable. It is preferable to use a tissue containing a cell required to obtain pathological information, such as a tumor tissue derived from the tissue which breaks a balance in an individual and dysfunctions in growth regulation. Examples thereof include extracted tissues for removal of malignant tumors from the cancer patients.

The cyclin-dependent kinase (CDK) is a generic term for various enzymes activated by binding to cyclin, and does not have an activity by itself, but becomes an activated form by binding to cyclin. The CDK acts in a specific phase of a cell cycle depending on its kind. Examples of CDK include CDK1, CDK2, CDK4, CDK6, cyclin A-dependent kinase, cyclin B-dependent kinase, and cyclin D-dependent kinase.

From plural kinds of CDKs listed herein, a first CDK and a second CDK are determined, and the expression levels and activity values of the first ODE and the second CDK of cells of the tissue collected from a cancer patient are measured.

The ODE activity value refers to kinase activity level (U) (unit is abbreviated as (U)) which is calculated from an amount of a substrate to be phosphorylated upon the binding of CDK to a specific cyclin. Examples of the substrate to be phosphorylated with the CDK include histone H1 for activated CDK1 and activated CDK2 as well as Rb (retinoblastoma protein) for activated CDK4 and activated CDK6. The CDK activity value can be measured by any conventional method of measuring CDK activity. For example, there is a method which includes preparing a sample containing activated CDK from a cell lysate of a measurement sample, then using the sample and $^{32}$P-labeled ATP ($\gamma$-[$^{32}$P]-ATP) so that a substrate protein is allowed to incorporate $^{32}$P, measuring the labeling amount of the phosphorylated substrate labeled with $^{32}$P, and quantitatively determining the activity values based on a standard curve previously prepared using standard samples. As a method using no labeling by radioactive substance, a method disclosed in Japanese Patent Application Laid-Open (JP-A) No. 2002-335997 is exemplified.

The method includes preparing a sample containing activated CDK of interest from a cell lysate of a subject, reacting the substrate with adenosine 5'-O-(3-thiotriphosphate) (ATP-$\gamma$S) to introduce monothiophosphate group into a serine or threonine residue in the substrate protein, labeling the substrate protein by binding a fluorescent substance or a labeled enzyme to a sulfur atom in the introduced monothiophosphate group, measuring the amount of the labeled thiophosphorylated substrate (or the amount of the fluorescent substance in the case where the fluorescent substance is used), and quantitatively determining the phosphoric acid amount based on a standard curve previously prepared using standard samples.

Samples subjected to activity measurement are prepared by specifically collecting CDK of interest from lysates of tissues containing cells to be measured. The sample may be prepared by using an anti-CDK antibody specific to CDK of interest. In the case where the activity of a specific cyclin-dependent kinase (for example, cyclin A-dependent kinase, cyclin B-dependent kinase or cyclin E-dependent kinase) is measured, the sample may be prepared using an anti-cyclin antibody. In both cases, CDK other than activated CDK is contained in the sample. For example, the cyclin-CDK complex to which a CDK inhibitor is bound is also contained in the sample. When the anti-CDK antibody is used, CDK itself, a complex of CDK and a cyclic complex and/or a CDK inhibitor, and complexes of CDK and other compounds are contained. Accordingly, CDK activity value is measured in terms of the unit (U) of the phosphorylated substrate under the condition where various CDKs such as activated CDK, inactivated CDK, and various competitive reactive substances co-exist.

The CDK expression level is an amount of target CDK (unit corresponding to the number of molecules), which is contained in a cell lysate obtained by suspending cells to be measured in a buffer solution, or the like, and can be measured by a known method of measuring the amount of a target protein in a protein mixture. For example, an enzyme-linked immunosorbent assay (ELISA) or a Western blot process may be used. Alternatively, the measurement can be performed by a method described in JP-A No. 2003-130871. The target protein (CDK) may be captured by using an antibody specific to the target protein. For instance, an anti-CDK1-antibody can be used to capture all CDK1s present in cells (CDK itself, a complex of a cyclin complex and/or a CDK inhibitor, and complexes of CDK and other compounds are contained).

The term "recurrence risk score" is a value obtained from the activity value and expression level of the first CDK and the second CDK. As the recurrence risk score, either the activity value or the expression level may be used alone or a value calculated by addition, subtraction, multiplication and division of the activity value and the expression level may be used. It is preferable to use a ratio of the activity value and the expression level. As the ratio of the activity value and the expression level, a value obtained by dividing the activity value by the expression level (activity value/expression level=specific activity), a value obtained by dividing the expression level by the activity value (expression level/activity value=reciprocal of specific activity), or the like can be used.

For example, as the recurrence risk score, values obtained based on Equations (5) to (7) below can be used. Recurrence risk score $$(RRS)=F(x)\times G(y) \quad (5)$$

$$F(x)=a/(1+\mathrm{Exp}(-(x-b)\times c)) \quad (6)$$

$$G(y)=d/(1+\mathrm{Exp}(-(y-e)\times f)) \quad (7)$$

(wherein a to f represent constants.)

In the above-mentioned equation, x represents the specific activity of the first CDK and y represents the specific activity ratio. Here, the CDK specific activity is represented as the CDK activity value/CDK expression level and the specific activity ratio is represented as the second CDK specific activity/first CDK specific activity.

Here, the reason that the recurrence risk score can be calculated from Equations (5) to (7) above will be described. First, the meanings of the CDK specific activity and specific activity ratio will be described.

The CDK specific activity is the ratio of the activity value to the expression level of CDK. The CDK specific activity is a parameter that reflects the CDK enzyme activity per unit CDK protein mass contained in a sample, corresponds to the ratio of active CDK to CDK occurring in cells, and shows the CDK activity level based on the proliferating state of tumor cells to be judged.

The specific activity ratio is the ratio of the second CDK specific activity to the first CDK specific activity. The CDK specific activity ratio is the ratio between the activity levels of two CDKs each exhibiting an activity in a specific cell cycle, and is a parameter that reflects which of the CDK activities in cancer patient's cells is predominant (how much the ratio of cell in each stage of cell cycle is).

Generally, since a cancer cell is out of normally controlled proliferation and proliferates rapidly, when the ratio of cells staying in the period between S phase (DNA replicative period) and G2 phase (period of from termination of DNA synthesis to initiation of mitotic division) is high, the cells can be estimated to become cancerous. The aneuploidy is considered to be caused by passing through an abnormal M phase (cell division stage), or proceeding to G1 phase and then S phase without undergoing M phase. Therefore, the sample in which the ratio of cells in M phase is low may be estimated to become cancerous.

Accordingly, it is preferable that for example, CDK1 showing an activity during shifting from G2 phase to M phase in cell cycle is used as the first CDK, and CDK2 showing an activity during shifting from G1 phase to S stage in cell cycle is used as the second CDK. By determining the CDK specific activity ratio based on these two CDKs, a numerical value reflecting how much the cells in the S or G2 phase occur relative to the cells in the M phase can be obtained. This numerical value can be used as a parameter showing the proliferation rate of the cells. That is, the recurrence risk score is a value used as a parameter showing the proliferation rate of the cells.

Then, Equations (5) to (7) for calculating the recurrence risk score will be described.

As illustrated above, parameters correlated with the proliferation rate of cells (risk of cancer recurrence) can be obtained by obtaining the CDK specific activity ratio based on the first CDK specific activity and the second CDK specific activity.

However, there can be cases where the CDK specific activity ratio is not correlated with the proliferation rate of cells when the CDK1 specific activity is abnormally high. For example, when the CDK specific activity ratio is determined by using CDK1 as the first CDK and CDK2 as the second CDK as illustrated above, the CDK specific activity ratio is low when the CDK1 specific activity is abnormally high. From another viewpoint, this low ratio can be also considered attributable to abnormal activation of CDK1 by high expression of cyclin that has formed a complex with CDK1. It is considered that even if the amount of CDK activated in a certain cell cycle is low, cells can proliferate by compensatory function of another specific CDK, so abnormal activation of specific CDK can be also considered attributable to abnormal cellular kinetics.

Accordingly, the risk of cancer recurrence is considered to be specified by two risk factors: (A) first CDK specific activity and (B) second CDK/first CDK specific activity ratio, so that the risk of cancer recurrence is evaluated based on these risk factors. The probabilities of cancer recurrence based on the risk factors (A) and (B) are expressed as risk score RS (A) and risk score RS (B) by using numerically evaluated scales. The probabilities of cancer recurrence resulting from the risk factors (A) and (B) are expressed as recurrence risk score RRS by using a numerically evaluated scale. Consequently, the probability of cancer recurrence, namely, recurrence risk, is given by a product obtained by multiplying the probability of cancer recurrence resulting from the risk factor (A) by the probability of cancer recurrence from the risk factor (B), and therefore, the recurrence risk score (RRS) is given by a value proportional to the product of the risk score RS (A) and the risk score RS (B).

Accordingly, Equation (8) below can hold:

$$RRS=RS(A) \times RS(B) \quad (8)$$

The risk score RS (A) and the risk score RS (B) can be determined in the following manner.

Figure 3A:
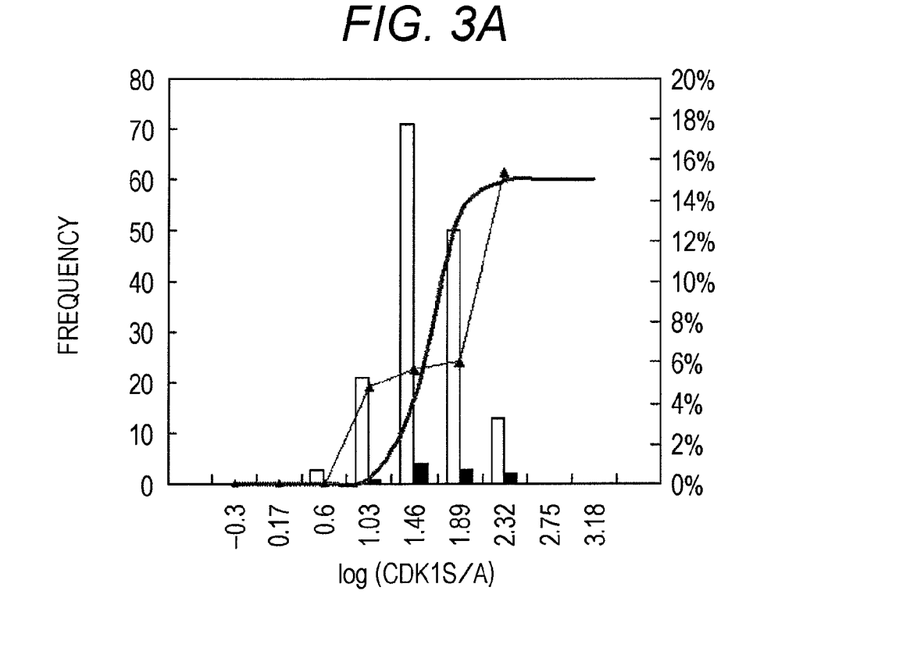
FIG. 3A is a histogram showing a relationship between CDK1 specific activity obtained from a plurality of cancer patients and the cancer recurrence rate and FIG. 3B is a histogram showing a relationship of the specific activity ratio between CDK1 and CDK2 obtained from a plurality of cancer patients and the cancer recurrence rate.
Figure 3B:
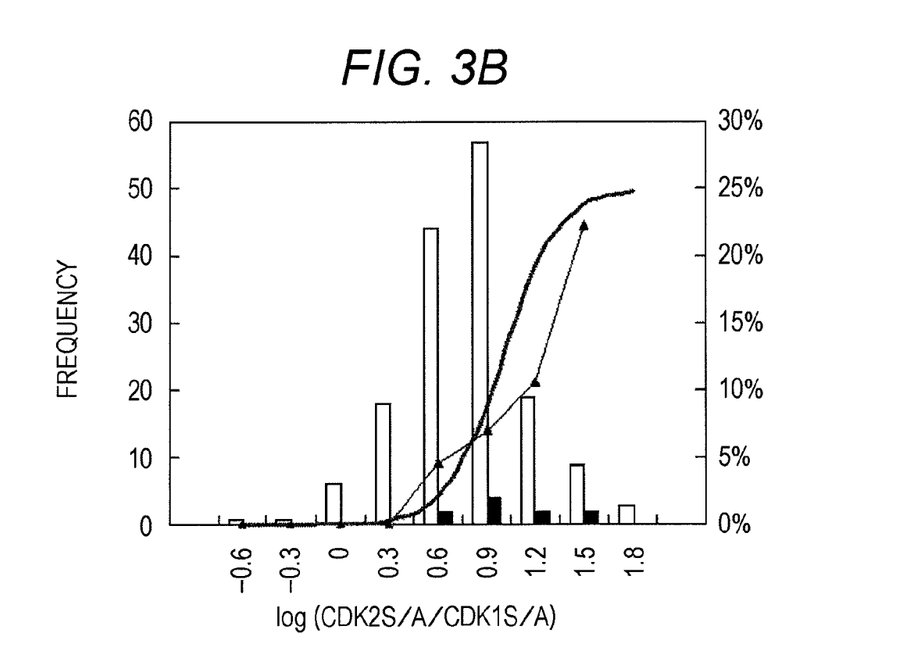

FIG. 3A is a histogram showing a relationship between CDK1 specific activity obtained from a plurality of cancer patients and the cancer recurrence rate and FIG. 3B is a histogram showing a relationship of the specific activity ratio between CDK1 and CDK2 obtained from a plurality of cancer patients and the cancer recurrence rate. In this graph, a plurality of cancer patients are classified according to the CDK1 specific activity or the CDK2/CDK1 specific activity ratio obtained from the cancer patients, and the total number of patients contained in each class is shown by a white bar, and the number of patients having recurrence contained in each class is shown by a shaded bar. Further, the probability of cancer recurrence (number of patients having recurrence/total number of patients) in each class is shown by a line graph.

As is apparent from the graph, the probability of cancer recurrence is flatly increased according to the CDK1 specific activity or the CDK2/CDK1 specific activity ratio. Therefore, the possibility of cancer recurrence in each class can be approximated, thereby giving risk score RS (A) having the CDK1 specific activity as risk factor and risk score RS (B) having the CDK2/CDK1 specific activity ratio as risk factor. Then, the probability of cancer recurrence in each class is approximated by logistic function wherein the CDK1 specific activity is expressed as x, and the CDK2/CDK1 specific activity ratio is expressed as y, and the risk score RS (A) and risk score RS (B) are obtained in Equations (9) and (10) below:

$$RS(A); F(x)=a/(1+\mathrm{Exp}(-(x-b) \times c)) \quad (9)$$

$$RS(B); G(y)=d/(1+\mathrm{Exp}(-(y-e) \times f)) \quad (10)$$

(wherein a to f represent constants.)

As described above, the recurrence risk score RRS is expressed by Equation (11) below to derive Equation (5).

$$RRS=F(x) \times G(y) \quad (11)$$

Ki67 is a protein which is not expressed within the cell in G0 phase of cell cycle, but is expressed in G1, S, G2, and M phases. A cell expressing this protein is in a proliferative stage (proliferative state). In the cells contained in tissues extracted from the cancer patients, it is suggested that there is a possibility that the extracted tissues became cancerous as the number of Ki67-expressing cells is larger. Thus, it is known that Ki67 can be used as a marker for cell proliferation and cell cycle.

The percentage of Ki67-expressing cells can be determined from the proportion of the number of Ki67-expressing cells among the cells contained in tissues extracted from the cancer patients. The number of Ki67-expressing cells can be determined by staining Ki67 in the cells using an antibody to be specifically bound to Ki67 to which a dye is attached and calculating the stained cells.

The percentage of Ki67-expressing cells to be determined from the proportion of the number of Ki67-expressing cells can be determined by dividing the number of Ki67-expressing cells by the number of the cells to be measured (Formula (12) below).

Percentage of Ki67-expressing cells=number of Ki67-expressing cells/number of cells to be measured×100 (12)

It is preferable that the percentage of Ki67-expressing cells is defined as a proportion of Ki67-expressing cells among the number of cells contained in tissues extracted in order to remove malignant tumors from the cancer patients.

As an example of a method of determining the percentage of Ki67-expressing cells, a process of subjecting the cells contained in tissues extracted from the cancer patients to immunological staining using an MIB antibody to be specifically bounded to Ki67 is listed. The immunological staining can be performed by a conventionally known method. Then, the stained cells are immobilized on a slide glass, so that the proportion of the number of the stained cells among the number of cells in measurement samples can be calculated by an image analyzing apparatus. It is preferable that the measurement samples are the tissues extracted in order to remove malignant tumors from the cancer patients.

The expression level of Ki67 is an amount of Ki67 (unit corresponding to the number of molecules) included in the cells contained in tissues extracted from the cancer patients and the expression level can be measured by a conventionally known method of measuring the protein amount of Ki67 from a protein mixture using an antibody specific to Ki67. The expression level of Ki67 can also be determined by staining Ki67 in the cells using an antibody to be specifically bound to Ki67 to which a dye is attached and measuring the staining intensity of the stained cells. Additionally, a gene expression level of ki67 in the cells can also be defined as an expression level of Ki67. This gene expression level of ki67 can be measured by a conventionally known gene expression analysis technique such as hybridization of polynucleotide, Northern blotting or RT-PCR to quantify mRNA expression.

The risk of cancer recurrence can be judged based on the activity value and expression level of the first CDK, the activity value and expression level of the second CDK, and the percentage of Ki67-expressing cells or the expression level acquired in the above-described manner. The risk of recurrence can be judged by comparing, for example, the recurrence risk score and the percentage of Ki67-expressing cells described above with the threshold value set in advance.

Specifically, the recurrence risk score of the cancer patients is compared with a first threshold value and the percentage of Ki67-expressing cells of the cancer patients is compared with a second threshold value. When the recurrence risk score of the cancer patients is higher than the first threshold value and the percentage of Ki67-expressing cells is higher than the second threshold value, the risk of recurrence can be judged as high.

When the recurrence risk score is lower than the first threshold value and the percentage of Ki67-expressing cells is lower than the second threshold value, the risk of recurrence may be judged as low. When the recurrence risk score is higher than the first threshold value, but the percentage of Ki67-expressing cells is lower than the second threshold value and when the recurrence risk score is lower than the first threshold value, but the percentage of Ki67-expressing cells is higher than the second threshold value, the risk of recurrence may be judged as medium.

The threshold value can be set by various methods. For example, in the recurrence risk score, as for each of tumor cells of tissues extracted from a plurality of cancer patients whose cancer malignancy has been judged by a pathologist, the recurrence risk score is calculated based on the equation of the recurrence risk score RSS, and a value to classify into two groups: a patient group with cancer recurrence and a patient group without cancer recurrence can be set as a threshold value. Alternatively, a plurality of threshold values may be set for different ranges of the risk of recurrence: high, medium, and low so as to evaluate the risk of cancer recurrence in stages.

As for the percentage of Ki67-expressing cells, the threshold value can be set in the same manner as described above. For example, as for each of tumor cells of tissues extracted from a plurality of cancer patients whose cancer malignancy has been judged by a pathologist, the percentage of Ki67-expressing cells is calculated based on Equation (12) above, and a value to classify into two groups: a patient group with cancer recurrence and a patient group without cancer recurrence can be set as a threshold value.

As for the expression level of Ki67, the threshold value can be set in the same manner as described above and the risk of cancer recurrence may be judged by comparing the recurrence risk score and the expression level of Ki67 with the threshold value set in advance.

Figure 1:
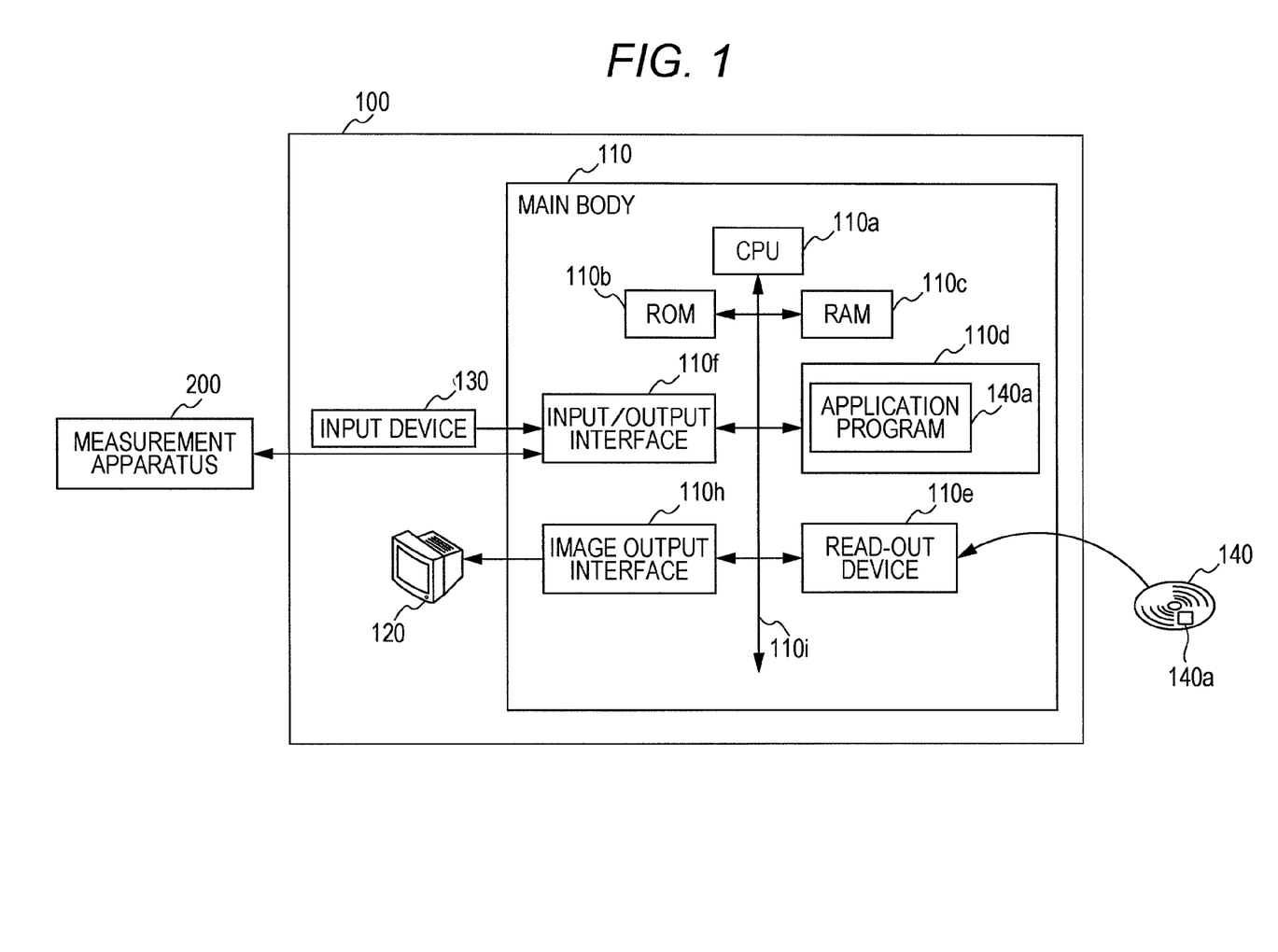
FIG. 1 is a view showing one embodiment in a computer which executes the judgment of risk of cancer recurrence.

Each step of the method of judging a risk of cancer recurrence in the embodiment can be performed in a computer. Hereinafter, a computer which is one embodiment for executing the method of judging a risk of cancer recurrence in the present invention is shown in FIG. 1.

A computer 100 is mainly configured by a main body 110, a display unit 120, and an input device 130. In the main body 110, a CPU 110$a$, a ROM 110$b$, a RAM 110$c$, a hard disk 110$d$, a read-out device 110$e$, and an input/output interface 110$f$, and an image output interface 110$h$ are data-communicably connected by a bus 110$i$.

The CPU 110$a$ can execute computer programs stored in the ROM 1101$b$ and the computer programs loaded in the RAM 110$c$.

The ROM 110$b$ is configured by mask ROM, PROM, EPROM, EEPROM, and the like, and is recorded with computer programs to be executed by the CPU 110$a$, data used for the same.

The RAM 110$c$ is configured by SRAM, DRAM, and the like. The RAM 110$c$ is used to read out the computer programs recorded on the ROM 110$b$ and the hard disc 110$d$. In executing the computer program, the RAM 110$c$ is used as a work region of the CPU 110$a$.

The hard disc 110$d$ is installed with various computer programs to be executed by the CPU 110$a$ such as operating system and application system program, as well as data used in executing the computer program. The application program 140$a$ to be described later is also installed in the hard disc 110$d$.

The read-out device 110$e$ is configured by flexible disc drive, CD-ROM drive, DVD-ROM drive, and the like, and is able to read out computer programs and data recorded on a portable recording medium 140. The application program 140$a$ according to the judgment of the computer is stored in the portable recording medium 140, so that the CPU 110$a$ can read out the application program 140$a$ from the portable recording medium 140 and install the application program 140$a$ to the hard disk 110$d$.

Operating system providing graphical interface environment such as Windows (registered trademark) manufactured and sold by US Microsoft Co. is installed in the hard disc 110$d$. In the following description, the application program 140$a$ according to the above-described judgment is assumed to be operating on the operating system.

The input/output interface 110$f$ includes a serial interface such as USB, IEEE1394, and RS-232C; a parallel interface such as SCSI, IDE, and IEEE1284; and an analog interface such as D/A converter and A/D converter. The input/output interface 110$f$ is connected to the input device 130 including a keyboard and a mouse, and users can use the input device 130 to input data into the main body 110 of the computer.

A measurement apparatus 200 which measures the activity value and expression level of CDK, the number of expressing cells in Ki67 and the number of cells to be measured is connected to the input/output interface 110$f$. Thus, the main body 110 of the computer can acquire the recurrence risk score calculated from the CDK1 specific activity and the CDK2/CDK1 specific activity and the percentage of Ki67- expressing cells calculated from the number of cells to be measured and the number of Ki67-expressing cells from the measurement apparatus 200 via the input/output interface 110f.

The image output interface 110h is connected to the display unit 120 configured by LCD, CRT, or the like, and is configured to output an image signal corresponding to the image data provided from the CPU 110a to the display unit 120. The display unit 120 outputs image data according to the input image signal. The display unit 120 outputs image data provided from the CPU 110a to be described later.

Figure 2:
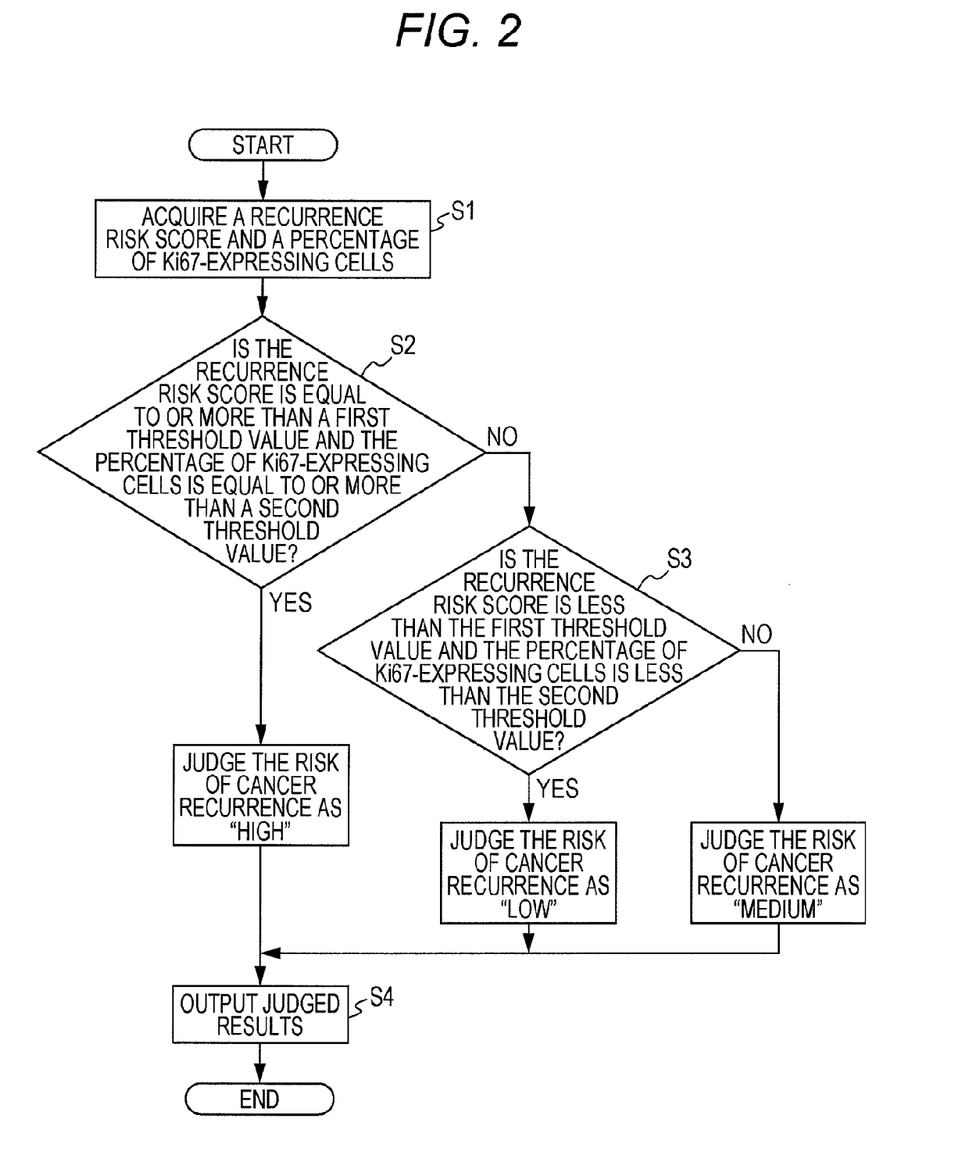
FIG. 2 is a view showing a flow of the judgment of risk of cancer recurrence.

FIG. 2 is a flow chary showing an operation of the application program 140a to execute the judgment of risk of recurrence of cancer.

When the activity value and expression level of CDK1, the activity value and expression level of CDK2, the number of Ki67-expressing cells, and the number of cells to be measured are acquired from the measurement apparatus 200 via the input/output interface 110f, the CPU 110a stores the activity value and expression level of CDK1, the activity value and expression level of CDK2, the number of Ki67-expressing cells, and the number of cells to be measured in the RAM 110c, respectively. The CPU 110a calculates the recurrence risk score and the percentage of Ki67-expressing cells from the activity value and expression level of CDK1, the activity value and expression level of CDK2, the number of Ki67-expressing cells, and the number of cells to be measured which are stored in the RAM 110c (step S1).

The CPU 110a reads out the first and second threshold values which has been stored in a memory 110d as data of the application program 140a in advance and executes the comparison of the first threshold value and the recurrence risk score with the second threshold value and the percentage of Ki67-expressing cells.

When the recurrence risk score is equal to or higher than the first threshold value and the percentage of Ki67-expressing cells is equal to or higher than the second threshold value, the risk of cancer recurrence is judged as "high" (step S2). When the recurrence risk score is less than the first threshold value or the percentage of Ki67-expressing cells is less than the second threshold value, the process is advanced to step S3.

In step S3, it is judged whether the recurrence risk score is less than the first threshold value and the percentage of Ki67-expressing cells is less than the second threshold value. When the recurrence risk score is less than the first threshold value and the percentage of Ki67-expressing cells is less than the second threshold value, the risk of cancer recurrence is judged as "low". In the cases other than the above-described case, the risk of cancer recurrence is judged as "medium".

The CPU 110a stores the judged results in the RAM 110c and outputs them on the display unit 120 via the image output interface 110h (step S4).

In the present embodiment, the activity value and expression level of CDK1, the activity value and expression level of CDK2, the number of Ki67-expressing cells, and the number of cells to be measured are acquired from the measurement apparatus 200 via the input/output interface 110f, however the present invention is not limited thereto. For example, the activity value and expression level of CDK1, the activity value and expression level of CDK2, the number of Ki67-expressing cells, and the number of cells to be measured may be acquired via the interface 110f by inputting from the input device 130.

In the present embodiment, the recurrence risk score and the percentage of Ki67-expressing cells are calculated from the activity value and expression level of CDK1, the activity value and expression level of CDK2, the number of Ki67-expressing cells, and the number of cells to be measured which are stored in the RAM 110c by the CPU 110a, however the present invention is not limited thereto. The recurrence risk score and the percentage of Ki67-expressing cells may be acquired from the measurement apparatus 200 via the input/output interface 110f. The recurrence risk score and the percentage of Ki67-expressing cells may be acquired via the interface 110f by inputting from the input device 130.

In the present embodiment, the risk of cancer recurrence is judged as "high", "low" or "medium", however the present invention is not limited thereto. The risk of cancer recurrence may be judged as "high" or "low". For example, when the recurrence risk score is equal to or higher than the threshold value and the percentage of Ki67-expressing cells is equal to or higher than the threshold value, the risk of cancer recurrence may be judged as "high". When the recurrence risk score is less than the threshold value or the percentage of Ki67-expressing cells is less than the threshold value, the risk of cancer recurrence may be judged as "low".

EXAMPLES

Example 1

Measurement of the Proliferation Rate of Cancer Cells Using the Activity Value of CDK Tumor-bearing mice were produced by transplanting breast cancer cell lines into nude mice subcutaneously. The tumors are extracted on Days 16 to 42 posttransplant, followed by measurement of the weight of each tumor and the specific activity ratio (SA) of CDK1 and CDK2.
(1) Production of Tumor-Bearing Mice 19 types of breast cancer cell lines were cultured in a $CO_2$ incubator at 37° C. and the cells were recovered (Ca. 70% confluency). The culture condition of each cell line is shown in Table 1.

Each of the recovered cell lines was suspended so as to be $1 \times 10^8$ cells/mL and two-fold diluted with high concentration Matrigel. Thereafter, 100 μL of the resulting suspensions were transplanted into the nude mice.

Each cell line was extracted on Days 16 to 42 posttransplant and the weight thereof was measured, followed by cryopreservation with liquid nitrogen. In this case, HCC1806 shown in Table 1 was extracted on Day 16 because of the fast proliferation rate, while other cell lines were extracted from the tumor cells whose size was reached a sufficient one during Days 28 to 42.

TABLE 1

| CELL NAME | BASAL MEDIUM | ADDITIVES |
|---|---|---|
| AU565 | DF12 | 10% FBS, 1% antibiotec-antimycotec |
| BT-20 | DF12 | 10% FBS, 1% antibiotec-antimycotec |
| BT-474 | DF12 | 10% FBS, 1% antibiotec-antimycotec |
| CAMA-1 | DF12 | 10% FBS, 1% antibiotec-antimycotec |
| HCC202 | DF12 | 10% FBS, 1% antibiotec-antimycotec |
| HCC1419 | DF12 | 10% FBS, 1% antibiotec-antimycotec |
| HCC1806 | DF12 | 10% FBS, 1% antibiotec-antimycotec |
| HCC1937 | DF12 | 10% FBS, 1% antibiotec-antimycotec |
| HCC1954 | DF12 | 10% FBS, 1% antibiotec-antimycotec |
| Hs 578T | DF12 | 10% FBS, 1% antibiotec-antimycotec |
| MCF7 | DF12 | 10% FBS, 1% antibiotec-antimycotec |
| MDA-MB-231 | DF12 | 10% FBS, 1% antibiotec-antimycotec |

TABLE 1-continued

| CELL NAME | BASAL MEDIUM | ADDITIVES |
|---|---|---|
| MDA-MB-435S | DF12 | 10% FBS, 1% antibiotec-antimycotec |
| MDA-MB-436 | DF12 | 10% FBS, 1% antibiotec-antimycotec |
| SK-BR-3 | McCoy's 5a | 10% FBS, 1% antibiotec-antimycotec, 200 mM L-glutamine |
| UACC-893 | DF12 | 10% FBS, 1% antibiotec-antimycotec |
| ZR-75-1 | DF12 | 10% FBS, 1% antibiotec-antimycotec |

The calculation was performed using a value obtained by dividing the weight of the extracted tumor cells by the number of days from when the tumor cells were transplanted to mice till when the cells were extracted as the proliferation rate. The recurrence risk score RRS in each cultivated cell was calculated simultaneously.

The calculated values are shown in Table 2.

TABLE 2

| CELL LINE | C2P RS | Log (TUMOR WEIGHT/ DAYS AFTER TRANSPLANT) |
|---|---|---|
| AU565 | 1.28 | 2.60 |
| BT20 | 0.83 | 1.35 |
| B1474 | 3.66 | 4.62 |
| CAMA-1 | 4.00 | 2.20 |
| Hcc1419 | 0.04 | 0.85 |
| Hcc1428 | 3.91 | 1.38 |
| Hcc1806 | 14.46 | 65.5 |
| Hcc1937 | 2.14 | 4.00 |
| Hcc1954 | 3.62 | 5.17 |
| Hcc202 | 0.85 | 0.95 |
| Hcc893 | 0.76 | 0.65 |
| Hs578T | 0.11 | 0.94 |
| MB231 | 7.01 | 26.8 |
| MB435s | 1.46 | 5.50 |
| MB436 | 8.65 | 8.34 |
| MCF7 | 1.98 | 5.17 |
| SKBr3 | 1.67 | 1.07 |
| T47D | 7.34 | 2.00 |
| ZR-75-1 | 1.64 | 3.56 |

(2) Measurement of Activity Values and Expression Levels of CDK1 and CDK2

Activity values and expression levels of CDK1 and CDK2 in the respective extracted tumor cells were measured.

"Preparation of Measurement Samples"

The extracted tumor cells were suspended in a buffer solution A (containing 0.1 w/v % Nonidet P-40 (Calbiochem), 50 mM Tris-HCL (pH 7.4), 5 mM EDTA, 50 mM sodium fluoride, 1 mM sodium orthovanadate, and 100 µl/ml protease inhibitor cocktail) at a concentration of tumor cells of about 150 mg/ml and the resulting suspension was put in a tube.

Then, the tumor cells in the tube were homogenized using an electric homogenizer. The tumor cells were crushed to prepare a cell lysate. Subsequently, the cell lysate was centrifuged at 15000 rpm at 4° C. for 5 minutes to give a supernatant for use as the measurement sample.

"Measurement of Expression Levels of CDK1 and CDK2"

50 µl of each measurement sample was put in each well of a blotter with a PVDF membrane (manufactured by Millipore) set thereon. Then, the measurement sample was suctioned from a bottom surface of the well, that is, a rear surface of the membrane, at a negative pressure of approximately 250 mmHg for approximately 30 seconds so that a protein in the measurement sample was adsorbed to the membrane. 100 µL of a washing solution B (containing 25 mM Tris-HCL (pH 7.4) and 150 mM NaCl) was put in each well which was then suctioned at a negative pressure of 500 mmHg for 15 seconds, thereby washing the membrane. After washing, 40 µL of a blocking reagent B (containing 4% BSA, 25 mM Tris-HCl (pH 7.4) and 150 mM NaCl) was put in each well and left stand for 15 minutes, and each well was suctioned at a negative pressure of 500 mmHg for 15 seconds, thereby blocking the membrane.

After blocking, 40 µl of a rabbit anti-CDK1 antibody (primary antibody) solution to be specifically bound to the CDK1 was put in each well and left stand at room temperature for approximately 30 minutes so that the CDK1 and the primary antibody in the membrane were reacted with each other. Then, the bottom surface of the well was suctioned at a negative pressure of 500 mmHg for 15 seconds. 100 µL of the washing solution B was put in each well which was then suctioned at a negative pressure of 500 mmHg for 15 seconds, thereby washing the membrane. 40 µL of a biotinylated anti-rabbit IgG-B antibody (secondary antibody) solution was put in each well and left stand at room temperature for approximately 30 minutes so that the primary antibody was reacted with secondary antibody in the membrane. Thereafter, the bottom surface of the well was suctioned at a negative pressure of 500 mmHg for 15 seconds. 100 µL of the washing solution B was put in each well which was then suctioned at a negative pressure of 500 mmHg for 15 seconds, thereby washing the membrane. 50 µL of a labeled solution containing FITC-labeled streptavidin was put in each well and left stand at room temperature for 30 minutes so that the secondary antibody in the membrane was FITC-labeled. Thereafter, the bottom surface of the well suctioned at a negative pressure of 500 mmHg for 15 seconds.

50 µL of the washing solution B was put in each well which was then suctioned at a negative pressure of 500 mmHg for 15 seconds; this operation was repeated 5 times so that the membrane was washed.

The membrane was detached from the blotter, rinsed with 20% methanol for 5 minutes and dried at room temperature for 20 minutes. Thereafter, the protein adsorbed to the membrane was analyzed and measured for its fluorescence intensity with a fluorescence image analyzer. The measurement value was calculated based on a calibration curve.

The calibration curve was prepared in the following manner: 50 µL of a solution obtained by dissolving recombinant CDK1 at five different concentrations in a washing solution B (containing 0.005% Nonidet P-40 and 50 µg/mL BSA) was put to each well treated previously in the same manner as described above, and then labeled with FITC in the same experimental procedure as described above, followed by measurement of the fluorescence intensity thereof, thereby expressing the relationship between the fluorescence intensity and the expression level of CDK1.

An expression level of CDK2 was determined in the same experimental procedure as described in the measurement of the expression level of CDK1 except that a rabbit anti-CDK2 antibody was used as the primary antibody in place of the rabbit anti-CDK1 antibody.

"Measurement of Activities of CDK1 and CDK2"

500 µl of the buffer A was put in a 1.5-ml Eppendorf tube, and the measurement sample was added thereto. The measurement sample was added to the tube such that the total protein mass in the resulting mixed solution in the tube reached 100 µg. 2 µg of the anti-CDK1 antibody and 20 µl of Sepharose beads coated with protein A were added thereto and left stand at 4° C. for 1 hour so that the CDK1 and the anti-CDK1 antibody were reacted with each other. After the reaction, the beads were washed 3 times with a beads washing buffer (containing 0.1 w/v % Nonidet P-40 and 50 mM Tris-HCl (pH 7.0)) and then suspended again in 15 μL of the lysis buffer A, whereby a sample containing Sepharose beads to which CDK1 was bound via the anti-CDK1 antibody was obtained.

10 μg of a CDK1 substrate solution (containing 10 μg histone H1, 5 mM ATP-γS (Sigma), 20 mM Tris-HCl (pH 7.4) and 0.1% Triton X-100) was added to the sample. The substrate solution was added to the tube such that the total amount of the mixed solution in the tube reached 50 μL. The mixture was shaken at 37° C. for 10 minutes to cause a kinase reaction, thereby introducing a monothiophosphoric acid group into the histone H1.

After the kinase reaction, the reaction mixture was centrifuged at 2000 rpm for 20 seconds to precipitate the beads, thereby recovering 18 μL of a supernatant. 15 μL of a binding buffer (containing 150 mM Tris-HCl (pH 9.2) and 5 mM EDTA) and 10 mM iodoacetylbiotin solution (containing 100 mM Tris-HCl (pH 7.5) and 1 mM EDTA) were added to the supernatant and left stand at room temperature in a dark place for 90 minutes, whereby the iodoacetylbiotin was bound to a sulfuric atom of the substrate (monothiophosphoric acid substrate) into which the monothiophosphoric acid group had been introduced. The reaction of the iodoacetylbiotin with the monothiophosphoric acid group was terminated by adding 2-melcaptoethanol. A sample containing 0.4 μg of the monothiophosphoric acid substrate to which the iodoacetylbiotin had been bound was blotted onto the PVDF membrane using a slot blotter.

The PVDF membrane was blocked with a solution containing 1 w/v % BSA, and streptavidin-FITC (Vector Laboratories, Inc.) was added thereto, and the mixture was reacted at 37° C. for 1 hour. After the reaction, the PVDF membrane was washed 3 times with 50 mM washing solution B. After the washing, the PVDF membrane was analyzed for its fluorescence with the fluorescence image analyzer. The activity value was calculated based on a calibration curve.

Here, the calibration curve can be created by serially diluting an active CDK1 recombinant molecule to obtain a sample and using the above-described measurement method. Therefore, 1 U (unit) activity of CDK1 to be measured is equivalent to the amount of fluorescence in the phosphorylated substrate given when the active recombinant molecule is about 1 ng.

The activity value of CDK2 was measured in the same manner as the measurement of the activity value of CDK1 except that the anti-CDK2 antibody and the active CDK2 recombinant molecule were used in place of the anti-CDK1 antibody and the active CDK1 recombinant molecule.

Figure 4:
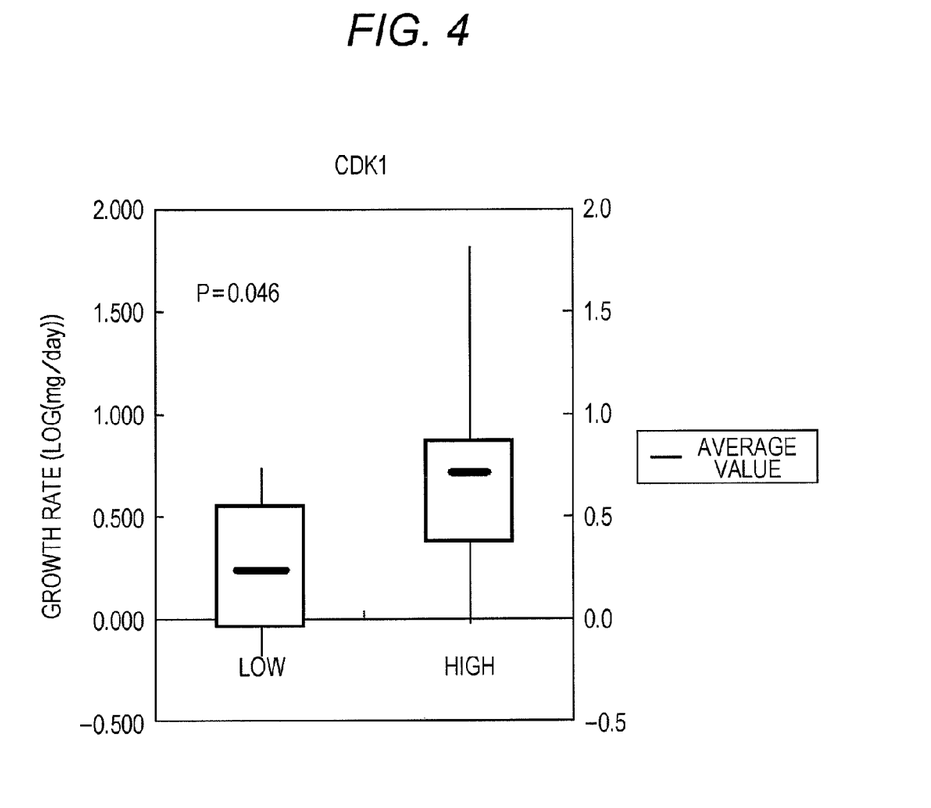
FIG. 4 is a graph showing results after comparing the proliferation rate with CDK1.
Figure 5:
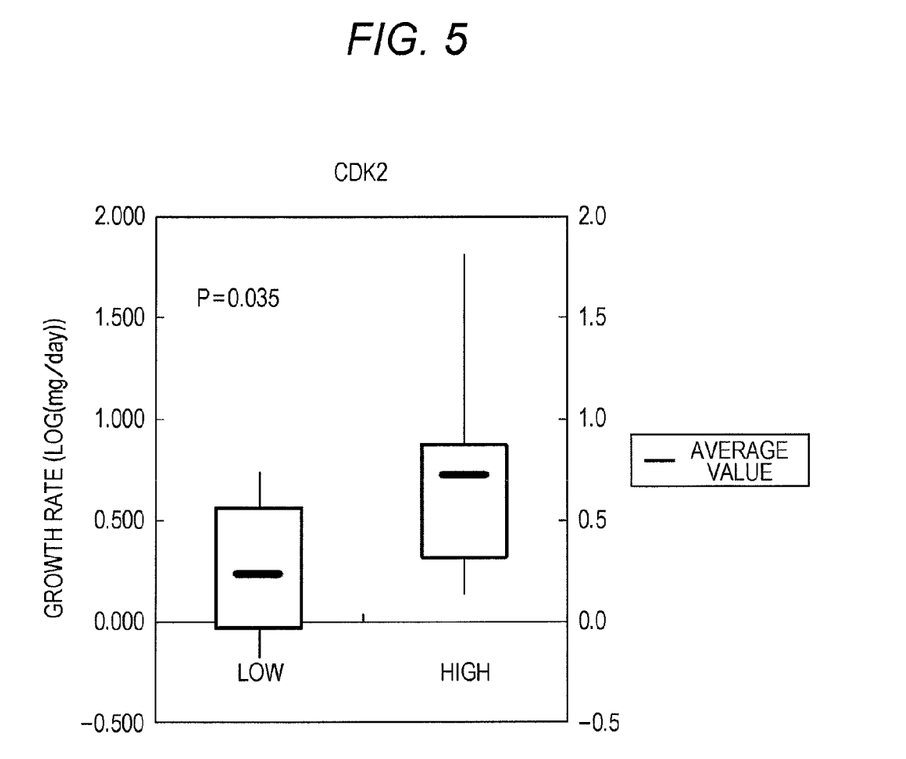
FIG. 5 is a graph showing a graph showing results after comparing the proliferation rate with CDK2.
Figure 6:
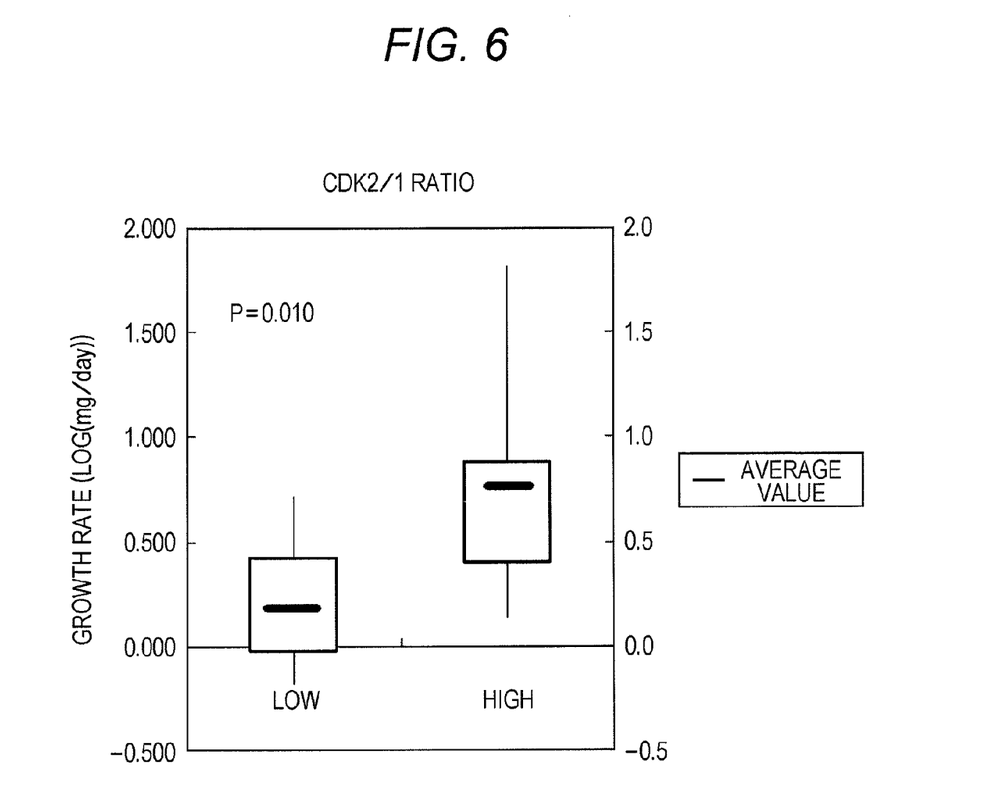
FIG. 6 is a graph showing results after comparing the proliferation rate with CDK2/CDK1.

The specific activity ratio of CDK1, the specific activity ratio of CDK2, and the specific activity ratio of CDK2/specific activity ratio of CDK1 (hereafter, the specific activity ratio is also referred to as SA) were calculated from the activity values and expression levels of CDK1 and CDK2 obtained after the measurement. Respective cell lines were classified into two groups at a median of respective parameters (SA of CDK1, SA of CDK2, and SA of CDK2/SA of CDK1) and the proliferation rate (tumor cell weight/number of days posttransplant) of each cell line was compared. The compared results are shown in Table 3. Further, the graphic results of respective parameters of Table 3 were each shown in FIG. 2 (CDK1), FIG. 3 (CDK2), and FIG. 4 (CDK2/CDK1).

TABLE 3

| PARAMETER | | N | PROLIFERATION RATE: MEANS ± S.D. [Log (mg/day)] | p value |
|---|---|---|---|---|
| CDK1 | ≥36 U | 9 | 0.706 ± 0.567 | 0.046 |
| | <36 U | 10 | 0.238 ± 0.342 | |
| CDK2 | ≥140 U | 9 | 0.717 ± 0.553 | 0.035 |
| | <140 U | 10 | 0.226 ± 0.348 | |
| CDK2/CDK1 | ≥3.0 | 9 | 0.762 ± 0.518 | 0.01 |
| | <3.0 | 10 | 0.176 ± 0.321 | |

The results show that the proliferation rate of a high parameter group is significantly higher than that of a low parameter group in each parameter as shown in Table 1 and FIGS. 1 to 3. This strongly suggests that SA of CDK1, SA of CDK2, and SA of CDK2/SA of CDK1 in the tumors reflect the proliferation rate of the tumors.

Example 2

Verification of the Method of Judging a Risk of Cancer Recurrence Based on the Number of Ki67-Expressing Cells and the Expression Level and Activity Value of CDK The judgment of the risk of recurrence in cancer patients using the judgment method according to the present embodiment was validated.

(1) Measurement of Activity Values and Expression Levels of CDK1 and CDK2

The expression levels and activity values of CDK1 and CDK2 in cells contained in respective mammary tissues extracted from 133 breast cancer patients who satisfied the conditions shown in Table 4 were measured. The expression levels and activity values of CDK1 and CDK2 in the cells were measured in the same manner as in Example 1 except that respective mammary tissues were used in place of the tumor cells.

TABLE 4

| CONDITIONS | |
|---|---|
| LYMPH NODE METASTASES | NEGATIVE |
| ENDOCRINE THERAPY | CARRYING OUT |
| CHEMOTHERAPY | NOT CARRYING OUT |
| HORMONE RECEPTOR | POSITIVE |

The recurrence risk score RRS was calculated using the obtained expression levels and activity values of CDK1 and CDK2 based on Equations (13) to (15) below:

$$RS1; F(x) = 0.15/(1 + \mathrm{Exp}(-(x-1.6) \times 7)) \quad (13)$$

$$RS2; G(y) = 0.25/(1 + \mathrm{Exp}(-(y-1.0) \times 6)) \quad (19)$$

$$RRS = 3000 \times F(x) \times G(y) \quad (15)$$

x = CDK1 activity value/CDK1 expression level
y = (CDK2 activity-value × CDK1 expression level)/(CDK2 expression-level × CDK1 activity value)

Subsequently, the recurrence risk score RRS obtained from each case was compared with the following conditions and the cancer patients were classified into two patient groups: a high risk recurrence group (High group) and a low risk recurrence group (Low group). As the classified result, the number of patients corresponding to the High group was 30, while the number of patients corresponding to the Low group was 103.

In each patient group, the number of patients whose cancer had recurred within five years was each 7 and 9 (Table 5).
High group: RRS≥3.0
Low group: RRS<3.0

TABLE 5

| GROUP | NUMBER OF PATIENTS | NUMBER OF PATIENTS RECURRED |
|---|---|---|
| High | 30 | 7 |
| Low | 103 | 4 |

(2) Measurement of the Number of Ki67-Expressing Cells

The proportion of the number of Ki67-expressing cells was measured using cells contained in respective mammary tissues extracted from the 133 breast cancer patients.

The measurement was performed by a method including labeling the extracted cells with the MIB antibody to Ki67 antigen, staining with an automatic immunostaining apparatus, and measuring the number of the stained cells in all the cells with an image analyzing apparatus.

The labeling with the MIB antibody was performed using Dako M7240, Monoclonal Mouse Anti-Human Ki-67 antigen (manufactured by Dako Co.). The stain detection was performed using Dako K4061, EnVision+DualLink (manufactured by Dako Co.) and Dako K3468, DAB+ (manufactured by Dako Co.) as an immunostaining detection kit.

The immunostaining was performed using S3400 Autostainer (manufactured by Dako Co.) as an automatic immunostaining apparatus and the image analysis was performed using ScanScope CS system (manufactured by Aperio Technologies, Inc.) and an image analysis software Nuclear v9. The above-described labeling, stain detection, and analysis were performed in accordance with the attached protocol.

As the result of image analysis, a specimen in which a proportion of the stained cell number to the measured cell number (a percentage of MIB positive cells) was 30% or more and a specimen in which the percentage of MIB positive cells was less than 30% were classified into a High risk group and a Low risk group, respectively. As the classified result, the number of patients corresponding to the High group was 54, while the number of patients corresponding to the Low group was 79. In each of the patient groups, the number of patients whose cancer had recurred within five years was each 8 and 3 (Table 6).

TABLE 6

| GROUP | NUMBER OF PATIENTS | NUMBER OF PATIENTS RECURRED |
|---|---|---|
| High | 54 | 8 |
| Low | 79 | 3 |

(3) Judgment of Risk of Recurrence

Specimens were classified into the High risk and the Low risk by combining the judgment of the risk of recurrence by the determined recurrence risk score based on CDK with the judgment of the risk of recurrence based on the number of Ki67-expressing cells. As with the judgment of the risk of recurrence based on the recurrence risk score and the judgment of the risk of recurrence based on the number of Ki67 expressing cells, a specimen judged as High, a specimen judged as Low, and other specimens were classified into a High risk group, a Low risk group, and an Int. risk group, respectively. The classified results are shown in Table 7.

TABLE 7

| GROUP | NUMBER OF PATIENTS | NUMBER OF PATIENTS RECURRED |
|---|---|---|
| High | 18 | 6 |
| Low | 67 | 2 |
| Int. | 48 | 3 |

As for the judgment of the risk of recurrence based on CDK (Table 5), the judgment of the risk of recurrence based on Ki67 (Table 6), and the judgment of the risk of recurrence based on CDK and Ki67 (Table 7) calculated in the above-described manner, a cumulative recurrence probability (p value) between the two groups classified into the High risk group and the Low risk group was analyzed by the Kaplan-Meier method. Further, a Hazard Ratio to be obtained by multivariate analysis using the proportional hazard model of Cox was also calculated. The P value shows significance probability between the two groups in a logrank test.

The calculated results of the cumulative recurrence probability and the hazard ratio in each judgment are shown in Table 8.

TABLE 8

| Parameter | | HR | p value |
|---|---|---|---|
| C2P | H vs L | 5.549 | 0.007 |
| Ki-67 | H vs L | 5.126 | 0.017 |
| Comb | HH vs LL | 12.319 | 0.002 |

As shown in Table 8, the cumulative survival rate of the group judged as Low risk in the judgment of the risk of recurrence based on CDK and Ki67 was significantly higher than those in the judgment of the risk of recurrence based on CDK and the judgment of the risk of recurrence based on Ki67.

The value of hazard ratio (HR) in the judgment of the risk of recurrence based on CDK and Ki67 is significantly higher than those in the judgment of the risk of recurrence based on CDK and the judgment of the risk of recurrence based on Ki67. This shows that the result of the judgment of the risk of recurrence based on CDK and Ki67 are much more reliable than those of the judgment of the risk of recurrence based on CDK and the judgment of the risk of recurrence based on Ki67.

What is claimed is:

1. A method for judging a risk of cancer recurrence comprising:
   acquiring an activity value and expression level of a first cyclin dependent kinase (CDK) of a cell contained in tissues extracted from cancer patients, an activity value and expression level of a second CDK, and a number of Ki67-expressing cells or an expression level of Ki67; and
   judging a risk of cancer recurrence based on the acquired activity value and expression level of the first CDK, the activity value and expression level of the second CDK, and a percentage of Ki67-expressing cells or the expression level of Ki67.

2. The method of claim 1, wherein
   judging the risk of cancer recurrence comprises:
     obtaining a recurrence risk score based on the activity value and expression level of the first CDK, and the activity value and expression level of the second CDK; and judging the risk of cancer recurrence based on the recurrence risk score and the percentage of Ki67-expressing cells or the expression level of Ki67.

3. The method of claim 2, wherein
the recurrence risk score is a value determined based on Equation (1) below:

$$RRS = F(x) \times G(y) \quad (1)$$

(wherein x represents a first CDK specific activity and the first CDK specific activity is expressed by a first CDK activity value/first CDK expression level; and
y represents a specific activity ratio and the specific activity ratio is expressed by a second CDK specific activity/first CDK specific activity).

4. The method of claim 3, wherein
F(x) and G (y) are Equations (2) and (3) below:

$$F(x) = a/(1 + \mathrm{Exp}(-(x-b) \times c)) \quad (2)$$

$$G(y) = d/(1 + \mathrm{Exp}(-(y-e) \times f)) \quad (3)$$

(wherein a to c represent constants defined from a correlation of x and a cancer recurrence rate, and d to f represent constants defined from a correlation of y and a cancer recurrence rate).

5. The method of claim 1, wherein
the percentage of Ki67-expressing cells is a value determined based on Equation (4):

Percentage of Ki67-expressing cells = number of Ki67-expressing cells/number of cells to be measured × 100 (4)

6. The method of claim 2, wherein
judging the risk of cancer recurrence comprises:
comparing the recurrence risk score with a first threshold value; and
comparing the percentage of Ki67-expressing cells with a second threshold value.

7. The method of claim 6, wherein
the risk of cancer recurrence is judged as high when the recurrence risk score is equal to or more than the first threshold value and percentage of Ki67-expressing cells is equal to or more than the second threshold value.

8. The method of claim 6, wherein
the risk of cancer recurrence is judged as low when the recurrence risk score is less than the first threshold value or the percentage of Ki67-expressing cells is less than the second threshold value.

9. The method of claim 1, wherein
the tissues extracted from cancer patients are mammary tissues.

10. A computer program product for enabling a computer to determine cancer recurrence, comprising:
a non-transitory computer readable storage medium; and
software instructions, on the non-transitory computer readable storage medium, for enabling the computer to perform predetermined operations, comprising:
acquiring an activity value and expression level of a first cyclin-dependent kinase (CDK) of a cell contained in tissues extracted from cancer patients, an activity value and expression level of a second CDK, and a number of Ki67-expressing cells or an expression level of Ki67; and
judging a risk of cancer recurrence based on the acquired activity value and expression level of the first CDK, the activity value and expression level of the second CDK, and the percentage of Ki67-expressing cells or the expression level of Ki67.

11. The computer program product of claim 10, wherein
judging the risk of cancer recurrence comprises:
obtaining a recurrence risk score based on the activity value and expression level of the first CDK and the activity value and expression level of the second CDK; and
judging the risk of cancer recurrence based on the recurrence risk score and the percentage of Ki67-expressing cells or the expression level of Ki67.

12. The computer program product of claim 11, wherein
the recurrence risk score is a value determined based on Equation (5) below:

$$RRS = F(x) \times G(y) \quad (5)$$

(wherein x represents a first CDK specific activity and the first CDK specific activity is expressed by a first CDK activity value/first CDK expression level; and
y represents a specific activity ratio and the specific activity ratio is expressed by a second CDK specific activity/first CDK specific activity).

13. The computer program product of claim 12, wherein
F(x) and G (y) are Equations (6) and (7) below:

$$F(x) = a/(1 + \mathrm{Exp}(-(x-b) \times c)) \quad (6)$$

$$G(y) = d/(1 + \mathrm{Exp}(-(y-e) \times f)) \quad (7)$$

(wherein a to c represent constants defined from a correlation of x and a cancer recurrence rate, and d to f represent constants defined from a correlation of y and the cancer recurrence rate).

14. The computer program product of claim 10, wherein
the percentage of Ki67-expressing cells is a value determined based on Equation (8):

Percentage of Ki67-expressing cells = number of Ki67-expressing cells/number of cells to be measured × 100 (8)

15. The computer program product of claim 11, wherein
judging the risk of cancer recurrence comprises:
comparing the recurrence risk score with a first threshold value; and
comparing the percentage of Ki67-expressing cells with a second threshold value.

16. The computer program product of claim 15, wherein
judging the risk of cancer recurrence as high when the recurrence risk score is equal to or more than the first threshold value and the percentage of Ki67-expressing cells is equal to or more than the second threshold value.

17. The computer program product of claim 15, wherein
judging the risk of cancer recurrence as low when the recurrence risk score is less than the first threshold value or the percentage of Ki67-expressing cells is less than the second threshold value.

18. A computer system adapted to determine cancer recurrence, comprising:
a processor, and
a memory, under control of said processor, including software instructions adapted to enable the computer system to perform operations comprising:
acquiring an activity value and expression level of a first cyclin-dependent kinase (CDK) of a cell contained in tissues extracted from cancer patients, an activity value and expression level of a second CDK, and a number of Ki67-expressing cells or an expression level of Ki67; and
judging a risk of cancer recurrence based on the acquired activity value and expression level of the first CDK, the activity value and expression level of the second CDK, and a percentage of Ki67-expressing cells or the expression level of Ki67.

19. The system of claim 18, wherein the judgment of cancer recurrence comprises:
obtaining a recurrence risk score based on the activity value and expression level of the first CDK and the activity value and expression level of the second CDK; and
judging the risk of cancer recurrence based on the recurrence risk score and the percentage of Ki67-expressing cells or the expression level of Ki67.

20. The system of claim 19, wherein
the recurrence risk score is a value determined based on Equation (9):

$$RRS = F(x) \times G(y) \quad (9)$$

(wherein x represents a first CDK specific activity and the first CDK specific activity is expressed by a first CDK activity value/first CDK expression level; and
y represents a specific activity ratio and the specific activity ratio is expressed by a second CDK specific activity/first CDK specific activity).

* * * * *